United States Patent
Liu et al.

(10) Patent No.: US 9,532,967 B2
(45) Date of Patent: Jan. 3, 2017

(54) USE OF PHENETHYL CAFFEATE DERIVATIVES IN THE PREPARATION OF A MEDICAMENT AGAINST TUMOR ANGIOGENESIS

(76) Inventors: Junyi Liu, Beijing (CN); Yansheng Du, Westfield, IN (US); Jirun Peng, Beijing (CN); Zhizhong Ma, Beijing (CN)

( * ) Notice: Subject to any disclaimer, the term of this patent is extended or adjusted under 35 U.S.C. 154(b) by 519 days.

(21) Appl. No.: 13/993,074

(22) PCT Filed: Dec. 8, 2011

(86) PCT No.: PCT/CN2011/083718
§ 371 (c)(1),
(2), (4) Date: Jul. 31, 2013

(87) PCT Pub. No.: WO2012/075957
PCT Pub. Date: Jun. 14, 2012

(65) Prior Publication Data
US 2013/0303611 A1    Nov. 14, 2013

(30) Foreign Application Priority Data
Dec. 10, 2010  (CN) .......................... 2010 1 0582759

(51) Int. Cl.
*A61K 31/216* (2006.01)
*A61K 31/222* (2006.01)
*A61K 31/235* (2006.01)

(52) U.S. Cl.
CPC ........... *A61K 31/216* (2013.01); *A61K 31/222* (2013.01); *A61K 31/235* (2013.01)

(58) Field of Classification Search
None
See application file for complete search history.

(56) References Cited

U.S. PATENT DOCUMENTS 5,981,583 A    11/1999   Aggarwal et al.
2013/0303611 A1    11/2013   Liu et al.

FOREIGN PATENT DOCUMENTS

CN    1810958 A    8/2006
CN    102198125 A    9/2011

OTHER PUBLICATIONS

Chun et al., Anticancer Activities of Substituted Cinnamic Acid Phenethyl Esters on Human Cancer Cell Lines, Journal of Chinese Pharmaceutical Sciences, 12( 4):184-187, 2003.*
Xia et al., Synthesis of trans-caffeate analogues and their bioactivities against HIV-I integrase and cancer cell lines, Bioorganic & Medicinal Chemistry Letters 18:6553-6557, 2008.*
International Search Report, dated Mar. 8, 2012 for International Application No. PCT/CN2011/083718, 5 pages.
Huang, Wencheng, The inhibition effect of caffeic acid phenethyl ester and analogue thereof for cancer transfer, Apiculture of China, 2006, vol. 57, No. 1, 1994-2011 China Academic Journal Electronic Publishing House, p. 45.
Li, Shuchun et al., Anticancer Activities of Substituted Cinnamic Acid Phenethyl Esters on Human Cancer Cell Lines, Journal of Chinese Pharmaceutical Sciences, 2003, vol. 12, No. 4, pp. 184-186.
Qian, Yiping et al., Structure-activity relationship for anti-haemolysis and cytotoxicity against HL-60 cells of caffeic acid phenethyl ester derivatives, Acta Biophysica Sinica, 2010, vol. 26, No. 4, pp. 294-300.
Verma, Rajeshwar P. et al., An Approach towards the Quantitative Structure-Activity Relationships of Caffeic Acid and its Derivatives, ChemBioChem, 2004, vol. 5, pp. 1188-1195.
Xia, Chunnian et al., Synthesis of trans-caffeate analogues and their bioactivities against HIV-1 integrase and cancer cell lines, Bioorganic & Medicinal Chemistry Letters, vol. 18, 2008, pp. 6553-6557.

* cited by examiner

*Primary Examiner* — Jeffrey S Lundgren
*Assistant Examiner* — Tori M Strong
(74) *Attorney, Agent, or Firm* — Lewis Roca Rothgerber Christie LLP

(57) ABSTRACT

Disclosed is the use of the compounds represented by formula (I) in the preparation of a medicament against tumor angiogenesis, wherein $R^1$ and $R^2$ are each independently $C_1$-$C_8$ alkylidene group or $C_2$-$C_8$ alkenylidene group; $A^1$ and $A^2$ are each independently aryl, isoaryl, or aryl or isoaryl optionally substituted by halogen, —CN, —$NO_2$, —OH, —SH, —$OR^3$, —$SR^3$, —$R^3$, —$R^3$—$OR^4$, —C(O)$R^3$, —S(O)$R^3$, —S(O)$_2R^3$, —$NR^4R^5$, —C(O)O$R^3$, —C(O)$NR^4R^5$, —O(O)C$R^4$, —S(O)C$R^4$ or —$NR^4$(O)C$R^5$, wherein $R^3$ is $C_1$-$C_4$ alkyl, $R^4$ and $R^5$ are each independently hydrogen, $C_1$-$C_4$ alkyl, aryl or substituted aryl; and X and Y are each independently oxygen; and the compound of formula (I) does not include phenethyl caffeate.

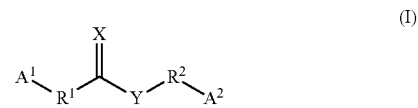

(I)

27 Claims, 2 Drawing Sheets

Control group    DMSO group    5μm group

10μm group    20μm group    50μm group    100μm group

Adminstration time (day)

USE OF PHENETHYL CAFFEATE DERIVATIVES IN THE PREPARATION OF A MEDICAMENT AGAINST TUMOR ANGIOGENESIS

CROSS-REFERENCE TO RELATED APPLICATION

This application is a National Phase Patent Application and claims the priority of International Application Number PCT/CN2011/083718 filed on Dec. 8, 2011, which claims priority of Chinese Patent Application No. 201010582759.7 filed on Dec. 10, 2010, the complete disclosures of both applications are incorporated herein by reference.

BACKGROUND OF THE INVENTION

1. Field of the Invention

The present invention belongs to the field of medicine, particularly relates to the use of phenethyl caffeate derivatives in the preparation of a medicament against tumor angiogenesis.

2. Description of the Related Art

Angiogenesis refers to the process of forming new vessels continuously based on the existing vessels of tissues. Angiogenesis under physiological conditions can be found in the processes of embryonic development and wound healing. Under pathological conditions, angiogenesis mainly exists in tumor and chronic inflammatory diseases. Inhibition of tumor angiogenesis not only can inhibit the growth and reproduction of tumor cells, but also has inhibitory effect on the metastasis and recurrence of the tumor (Carmeliet P, Jain R K. 2000. Angiogenesis in cancer and other diseases. Nature, 407 (6801): 249-57).

Since the world's first anti-angiogenic drug (bevacizumab, with trade name of Avastin and produced by Genentech Inc. in USA) was approved by U.S. FDA for the treatment of tumor in 2004, in just a few years, there has been a dozen of such drugs, which have been approved respectively for marketing internationally in a number of countries. The number of drugs studied in Phase II or III clinical trial is more than 50 (Folkman J. 2007. Angiogenesis: an organizing principle for drug discovery? Nature Review Drug Discovery. 6(4): 273-86). The world's pharmaceutical giants have focused on the research and development of such drugs as such drugs can inhibit the growth of tumor effectively, have significantly-reduced toxic and side effects on patients compared to radiation and chemotherapy drugs, and can also inhibit the metastasis of tumor. Therefore, research and application of angiogenesis inhibitors provides a new anti-cancer means and way for clinical patients.

However, currently the main target of the drugs resisting rumor angiogenesis is the endothlial cell (EC) of the new vessel. Although damaging to endothlial cells can inhibit angiogenesis, the normal vessels of the body (non-tumor vessels) is also damaged inevitably, especially when patients suffering from tumor also have atherosclerosis, the drug with the vascular endothlial cell as a target often inevitably results in damaging to the vessels, inducing complications which threaten the life of patients, such as thrombosis. In fact, patients with tumor are often elderly, and the elderly are the high-risk group suffering from atherosclerosis. Thus, these side is effects of the existing drugs resisting tumor angiogenesis limit their clinical application.

Study found that, besides endothlial cells, there are other factors affecting the formation of vessels during the process of tumor angiogenesis, such as pericytes and matrix proteins required for angiogenesis, both of which are indispensable factors affecting tumor angiogenesis. Therefore, it is of important social significance and economic value to development a medicament which can inhibit tumor angiogenesis, without potentially inducing thrombosis in normal non-tumor tissues.

SUMMARY OF THE INVENTION

Therefore, the object of the present invention is to provide a medicament, which can inhibit tumor angiogenesis, without inducing thrombosis due to damaging to endothlial cells.

The technical solution for achieving the above object is as follows:

The present invention provides use of a compound of formula (I) in the preparation of a medicament against tumor angiogenesis

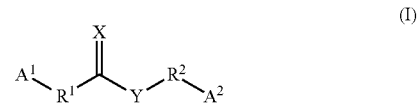

wherein $R^1$ and $R^2$ are each independently $C_1$-$C_8$ alkylidene group or $C_2$-$C_8$ alkenylidene group;

$A^1$ and $A^2$ are each independently aryl, isoaryl, or aryl or isoaryl optionally substituted by halogen, —CN, —NO$_2$, —OH, —SH, —OR$^3$, —SR$^3$, —R$^3$, —R$^3$—OR$^4$, —C(O)R$^3$, —S(O)R$^3$, —S(O)$_2$R$^3$, —NR$^4$R$^5$, —C(O)OR$^3$, —C(O)NR$^4$R$^5$, —O(O)CR$^4$, —S(O)CR$^4$ or —NR$^4$(O)CR$^5$, wherein $R^3$ is $C_1$-$C_4$ alkyl, and $R^4$ and $R^5$ are each independently hydrogen, $C_1$-$C_4$ alkyl, aryl or substituted aryl; and X and Y are each independently oxygen; and the compound of formula (I) does not comprise phenethyl caffeate.

In the above formula (I), $R^1$ may be $C_2$-$C_8$ alkenylidene group, preferably $C_2$-$C_3$ alkenylidene group, more preferably —CH═CH—.

In the above formula (I), $R^2$ may be $C_1$-$C_8$ alkylidene group, preferably $C_1$-$C_3$ alkylidene group, more preferably —CH$_2$—CH$_2$—.

In the above formula (I), $A^1$ and $A^2$ may be each independently aryl, or aryl optionally substituted by halogen, —CN, —OR$^3$, —SR$^3$, —R$^3$, —R$^3$—OR$^4$, —O(O)CR$^4$ or NR$^4$(O)CR$^5$; preferably, $A^1$ and $A^2$ may be each independently phenyl, or phenyl optionally substituted by —O(O)CR$^4$; and most preferably, $A^1$ may be 3,4-diacetyl phenyl, $A^2$ may be phenyl.

Examples of the compound of formula (I) are as follows:

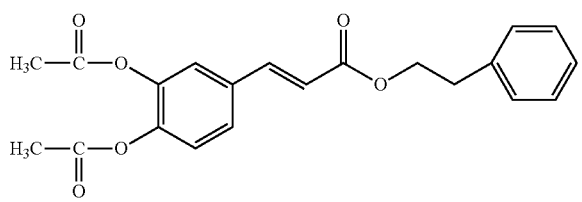

3,4-diacetyl phenethyl caffeate 3,4-diacetyl phenethyl caffeate is white fine crystal, with molecular formula of $C_{21}H_{20}O_6$, molecular weight of 368.40 g/mol, melting point of 82~83° C.

Other specific compounds for realizing the object of the present invention are as follows:

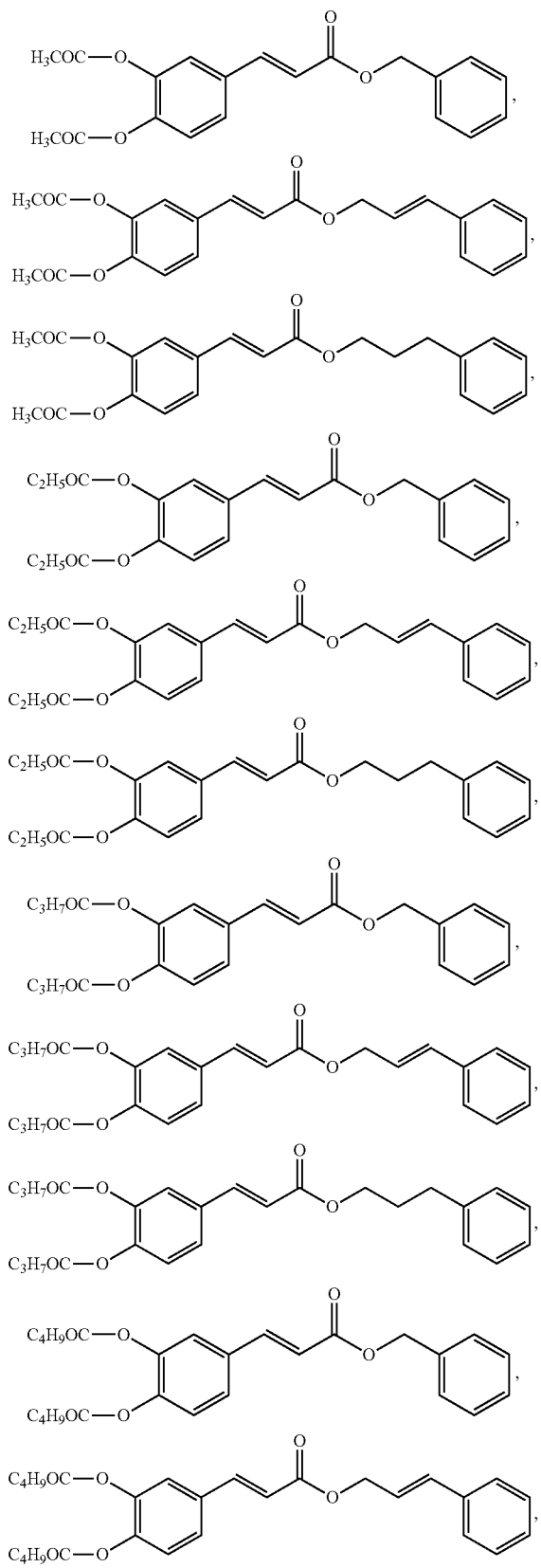

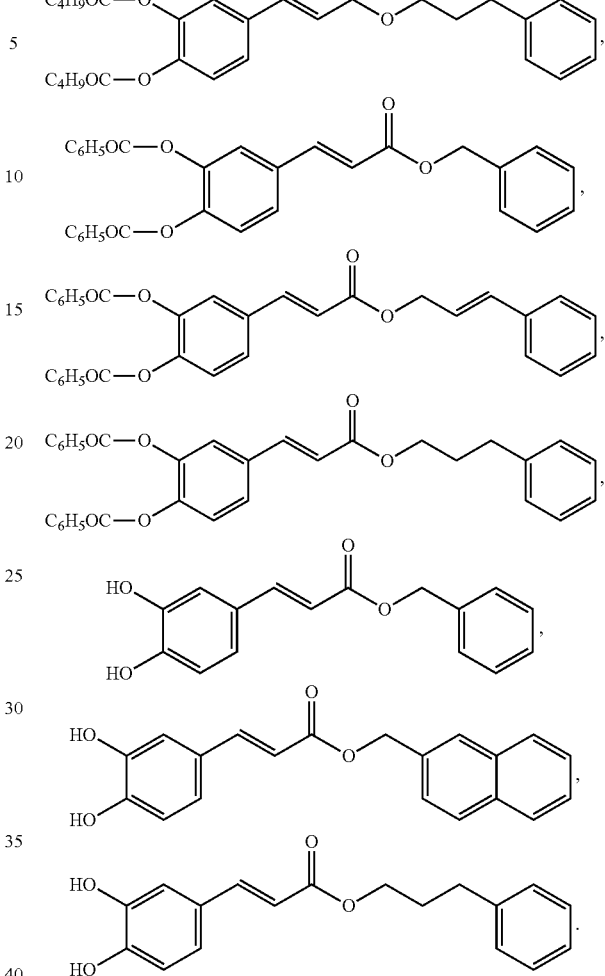

In the above use, the tumor may include various kinds of solid primary tumors, metastatic tumors or recurrent tumors.

The compound of formula (I) provided by the present invention can be used for inhibiting the formation of the new tumor vessels, and used for inhibiting the growth and/or metastasis and recurrence of the tumor effectively, therefore the compound of formula (I) can be used for treating neoplastic disease.

It is found through pharmacological tests that, the compound of formula (I) in the present invention, such as 3,4-diacetyl phenethyl caffeate has an important function of inhibiting tumor angiogenesis, and the compound realizes the function of inhibiting tumor angiogenesis mainly through inhibiting vessel pericytes formed by stem cells as well as synthesis and secretion of perivascular matrix protein, instead of through inhibiting vascular endothelial cells of the tumor. Therefore, the compound of the present invention is of high clinical application value and good development prospect, and can be used for the prevention and/or treatment of neoplastic diseases (such as various kinds of primary or metastatic neoplastic diseases) and control of progression of neoplastic diseases.

Based on the above research results, the present invention further provides the use of the compound of formula (I) in the preparation of a medicament for preventing and/or treating the tumor and its related diseases. The tumor may include various kinds of solid primary tumors, metastatic tumors or recurrent tumors.

Compared with the prior art, the present invention at least has the following beneficial effects:

The compound of formula (I) in the present invention realizes inhibition on tumor angiogenesis by inhibiting pericytes of the tumor vessels as well as synthesis and secretion of perivascular matrix protein. The target of the medicament of the present invention is out of the vessel lumen, while the thrombus is formed in the vessel lumen. Therefore, the compound of the present invention can inhibit tumor angiogenesis, without potentially inducing thrombosis due to damaging to endothelial cells, thus is of important social significance and economic value.

Phenethyl caffeate with concentrations of 50-100 μM shows no inhibitory effect on tumor angiogenesis mediated by pericytes, while the diacetyl phenethyl caffeate with the same concentrations shows significant inhibitory effect on tumor angiogenesis.

BRIEF DESCRIPTION OF THE DRAWINGS

The embodiments of the present invention will be illustrated in detail in combination with the accompanying drawings, wherein.

DETAILED DESCRIPTION OF THE EMBODIMENTS

The present invention will be further described in detail in combination with embodiments. It should be noted that the embodiments provided are only used to illustrate the present invention, rather than limit the scope of the present invention.

Embodiment 1 Inhibition of 3,4-diacetyl phenethyl caffeate on the formation of vessel network in vitro First, we constructed a vessel network model formed by culturing adult stem cells and vascular endothlial cells together. Adult stem cells have the function of differentiating into pericytes, and can secrete cytokines required for angiogenesis to promote the formation of new vessels. The isolated and cultured adult stem cells were cultured using EGM medium for 3-6 generations to be used. The isolated and cultured human endothelial cells were derived from the cord blood of healthy infants (38-40 weeks), in which monocytes were removed by gradient centrifugation, and the cells were cultured in EGM medium to obtain primary vascular endothlial cells, and 4-8 generations were applied after passage. The adult stem cells were implanted into a cell culture dish, maintaining cell density of $6 \times 10^6/cm^2$, and the vascular endothlial cells were implanted on the trophoblast cells of the adult stem cells after the adult stem cells were incubated at 37° C., 5% $CO_2$ for 3 hours, and the cell density of the vascular endothlial cells reached $1 \times 10^6/cm^2$. The two kinds of cells were co-cultured for six days, then the formation of tubular networks was observed, and the new vessel networks were labeled through CD31 fluorescence staining and horseradish peroxidase staining.

Figure 1:
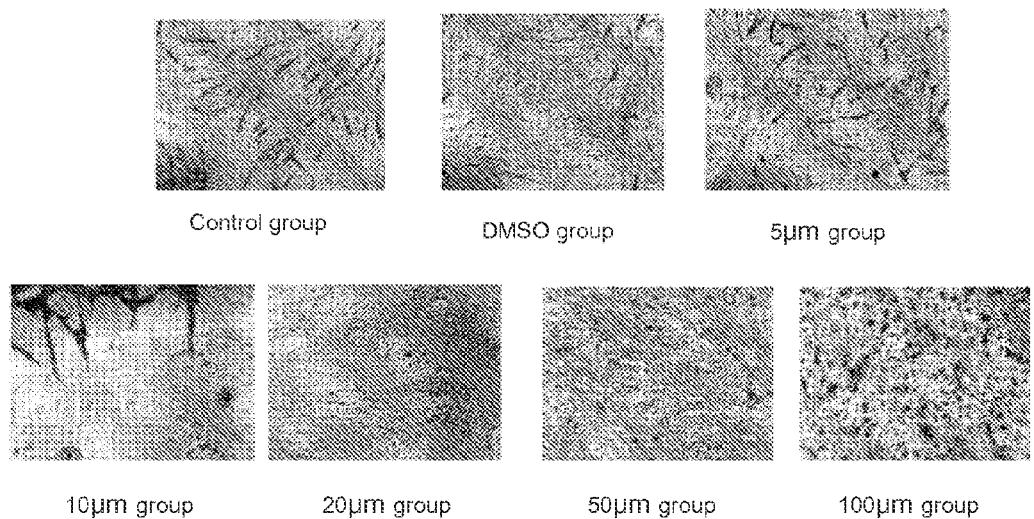
FIG. 1 illustrates the inhibition of 3,4-diacetyl phenethyl caffeate on the formation of vessel network in vitro; wherein following groups are provided: control group: this group is the blank control group, that is, no drugs or vehicles were added into the vessel network model cultured in vitro; DMSO group: in this group, the same amount of vehicle of dimethyl sulfoxide (DMSO) was added into the vessel network model cultured in vitro, i.e. Vehicle group; 5 μM group, 10 μM group, 20 μM group, 50 μM group and 100 μM group: in these groups, the compound 3,4-diacetyl phenethyl caffeate was respectively added into the vessel network models cultured in vitro, to obtain a final concentration of 5 μM, 10 μM, 20 μM, 50 μM and 100 μM.

Different doses of 3,4-diacetyl phenethyl caffeate (prepared according to conventional chemical method by the Laboratory of Peking University Health Science center) were co-cultured with the in vitro vessel network system. Through analysis by SPSS 16.0 software One-Way, it is found that the number and length of the formed vessel networks are significantly reduced as the doses of the derivatives were increased. The experimental results are shown in FIG. 1. By comparing the lengths of the formed vessel networks (Total Tube Length, TL) of the control group, DMSO group and 5 μm group ($2.850 \pm 0.689$ mm/mm$^2$, $2.47 \pm 0.534$ mm/mm$^2$, $2.802 \pm 0.212$ mm/mm$^2$), it is found that there is no significant difference among the three groups ($P>0.05$); and by comparing the TLs of the 10 μm group, 20 μm group, 50 μm group and 100 μm group ($0.874 \pm 0.117$ mm/mm$^2$, $0.337 \pm 0.89$ mm/mm$^2$, $0.084 \pm 0.032$ mm/mm$^2$, $0.0054 \pm 0.002$ mm/mm$^2$), it is found that there are significant differences among the four groups ($P<0.05$). By comparing the numbers of branchs (NB) of the vessels of the control group, DMSO group and 5 μm group ($5.97 \pm 0.61$/mm$^2$, $5.76 \pm 0.71$/mm$^2$, $6.12 \pm 0.48$/mm$^2$), it is found that there is no significant difference among the three groups ($P>0.05$); and by comparing the NBs of the 10 μm group, 20 μm group, 50 μm group and 100 μm group ($1.55 \pm 0.17$/mm$^2$, $0.50 \pm 0.063$/mm$^2$, $0.13 \pm 0.026$/mm$^2$, $0.04 \pm 0.001$/mm$^2$), there are significant differences among the four groups ($P<0.05$). However, there is no significant difference among the total numbers of ECs of CD31+ in respective groups. The total numbers of ECs in the control group, DMSO group, 5 μm group, 10 μm group, 20 μm group, 50 μm group and 100 μm group are $7.52 \pm 1.24$/mm$^2$, $8.66 \pm 1.31$/mm$^2$, $8.87 \pm 1.59$/mm$^2$, $6.0 \pm 1.72$/mm$^2$, $6.22 \pm 1.42$/mm$^2$, $952 \pm 1.34$/mm$^2$, $8.33 \pm 0.79$/mm$^2$ respectively, and there is no significant difference among respective groups through analysis.

Thus it can be seen that 3,4-diacetyl phenethyl caffeate has an inhibitory effect on the formation of vessel networks in vitro.

Embodiment 2 Inhibition of 3,4-diacetyl phenethyl caffeate on the growth of tumors of BALB/c nude mice inoculated with cells of human hepatocellular carcinoma BEL-7402 cell lines in vivo First, $1 \times 10^6$ cells of human hepatocellular carcinoma BEL-7402 cell lines were injected subcutaneously (sc) into the forelimbs of BALB/c male nude mice, and the mice with tumor were killed after the tumor was formed, the skin of the mice was cut off, and the complete tumor tissue was separated and removed, and then immersed into physiological saline and cut into pieces with diameter of 2 mm. The tumor tissue pieces were implanted subcutaneously into the forelimbs of nude mice in another group for drug experiments. The nude mice with tumor were randomly divided equally into an experimental group and control group, with 10 mice in each group. For the experimental group, CMC solution of 5‰compound of formula (I) was administrated to the mice with tumor in the experimental group by gavage at a dose of 20 mg/kg, while the mice in the control group were fed with control solution. The mice were administrated for the first six days continuously every week, with no administration at the 7th day, and the administration was kept for 3 weeks; and for the control group, the control solution was administrated to the mice by gavage, and the administration time is the same as that of the experimental group. Experimental data, such as tumor size (i.e., long diameter a and short diameter b), experimental animal weight (g), etc., were recorded regularly, and photographs were taken. Measurement result was recorded every time, and the tumor volume and the ratio of tumor volume to tumor weight were calculated for each animal based on the measurement results.

Figure 2:
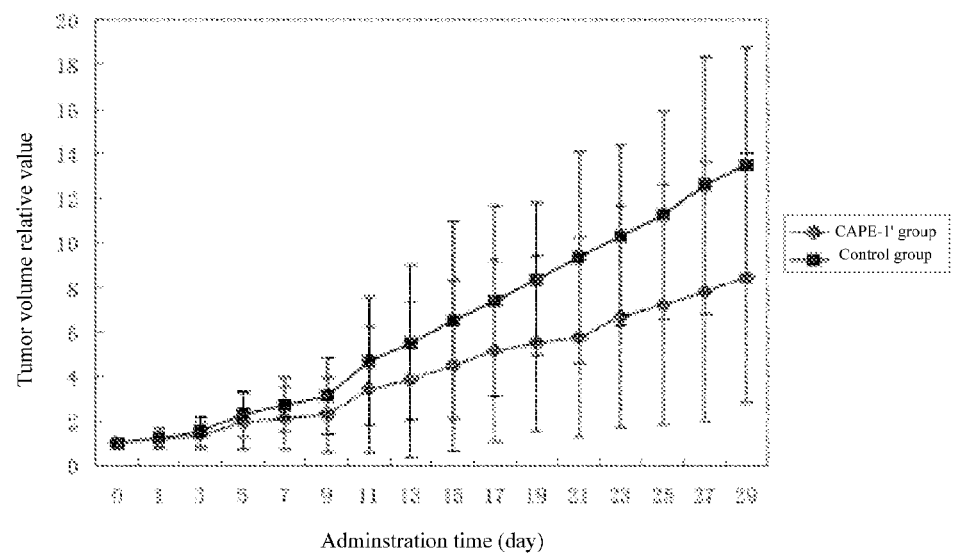
FIG. 2 illustrates the inhibition of 3,4-diacetyl phenethyl caffeate on the growth of tumors of BALB/c nude mice inoculated with cells of human hepatocellular carcinoma BEL-7402 cell lines in vivo; wherein following groups are provided: control group: in this group, the same amount of control solution was added, and the ratio of tumor volume to tumor weight was detected after three weeks; experimental group (CAPE-1' group): in this group, the BALB/c nude mice were daily fed with the compound 3,4-diacetyl phenethyl caffeate after the mice were inoculated with cells of human hepatocellular carcinoma BEL-7402 cell lines in vivo, and the ratio of tumor volume to tumor weight was detected after three weeks.

Formula for calculating the tumor volume is: v=a×b2/2 (a represents the long diameter of the tumor and b represents the short diameter of the tumor, which are in unit of mm; and V is calculated in unit of mm³). Formula for calculating the ratio of tumor volume to tumor weight is: p=v/w (v represents the volume, which is in unit of mm³; w represents the weight of the mouse, which is in unit of g; p is in unit of mm³/g). The results are shown in FIG. 2 (CAPE-1' group is the experimental group). For the control group, the average tumor volume of the mice is increased rapidly after the incubation period (9 days); and for the experimental group, the average tumor volume of the mice is maintained at the original level, with no significant changes, as shown in FIG. 2. FIG. 2 shows comparison of changes of tumor volumes between the experimental group and control group. The horizontal axis represents the number of days for administration, and the vertical axis represents the tumor volume relative value of the mice with tumor (=tumor volume measured value/tumor volume measured value which is measured at the first day of administration).

The experimental results show that 3,4-diacetyl phenethyl caffeate has an inhibitory effect on the growth of tumors of BALB/c nude mice inoculated with cells of human hepatocellular carcinoma BEL-7402 cell lines in vivo.

Embodiment 3 Inhibition of phenethyl caffeate on tumor angiogenesis mediated by pericytes of vessels We constructed an angiogenesis model by culturing stromal cells and vascular endothlial cells (ECs) together. Stromal cells and endothlial cells were graciously provided by Vascular Biology Medical Center of Medical School of the State University in Indiana. The stromal cells were implanted into a cell culture dish, maintaining cell density of 6×10⁶/cm², and ECs were implanted on the trophoblast cells of the stromal cells after the stromal cells were incubated in the EBM-2/5% FBS culture medium for 3 hours, with cell density of ECs reaching 1×10⁶/cm². The two kinds of cells were co-cultured in EBM-2/5% FBS culture medium for six days, then the formation of tubular vessels was observed, and EC vessels were labeled through CD31 fluorescence staining and horseradish peroxidase staining.

Then, the inhibition of compounds phenethyl caffeate and 3,4-diacetyl phenethyl caffeate with concentrations of 50-100 μM on tumor angiogenesis mediated by pericytes was studied. The results are shown in Table 1 and FIG. 3.

TABLE 1

| | Length of the formed vessel network (Total Tube Length, TL, n = 8) | |
|---|---|---|
| | phenethyl caffeate (CAPE) | 3,4-diacetyl phenethyl caffeate (I) |
| control | 436 ± 41 | 436 ± 29 |
| 50 μM | 332 ± 24 | 114 ± 20 |
| 100 μM | 314 ± 27 | 20 ± 11 |

Figure 3:
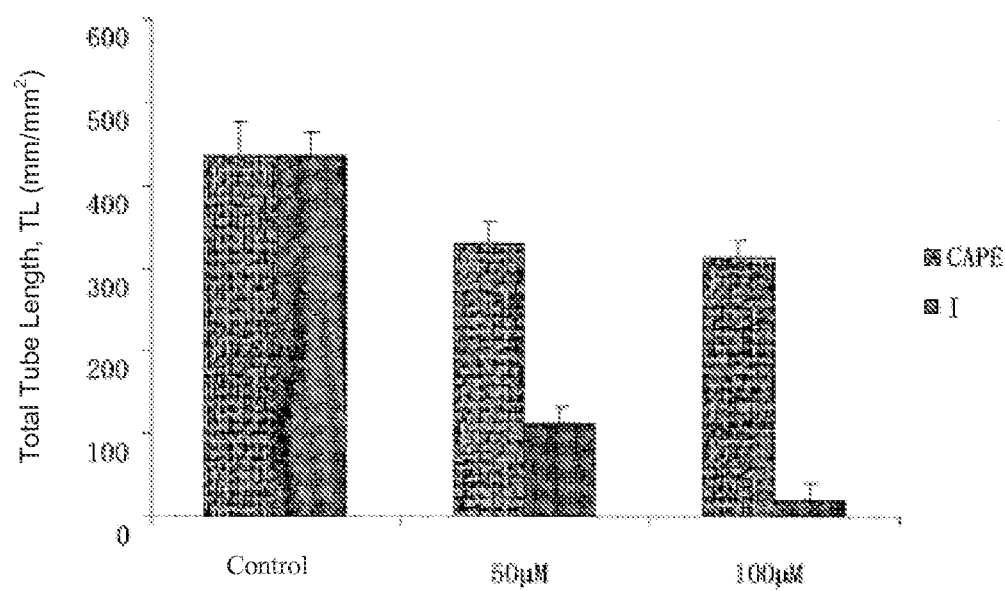
FIG. 3 illustrates the inhibition of compounds phenethyl caffeate and 3,4-diacetyl phenethyl caffeate on tumor angiogenesis mediated by vessel pericytes.

It can be seen from Table 1 and FIG. 3 that, 3,4-diacetyl phenethyl caffeate with concentrations of 50-100 μM has an inhibitory effect on tumor angiogenesis mediated by pericytes; while phenethyl caffeate with concentrations of 50-100 μM shows no inhibitory effect on tumor angiogenesis mediated by pericytes.

Thus, it is indicated that 3,4-diacetyl phenethyl caffeate of the present invention has a better inhibitory effect on the inhibition of tumor angiogenesis.

What is claimed is:

1. A method for inhibiting tumor angiogenesis, comprising administering to a subject a therapeutically effective amount of a compound of formula (I):

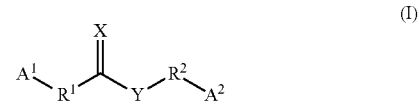

wherein $R^1$ and $R^2$ are each independently $C_1$-$C_8$ alkylidene group or $C_2$-$C_8$ alkenylidene group;
$A^1$ is 3,4-diacetyl phenyl, and $A^2$ is phenyl; and
X and Y are each independently oxygen; and the compound of formula (I) does not comprise phenethyl caffeate.

2. The method according to claim 1, wherein the tumor comprises solid primary tumors, metastatic tumors or recurrent tumors.

3. The method according to claim 1, wherein $R^1$ is a $C_2$-$C_8$ alkenylidene group.

4. The method according to claim 1, wherein $R^1$ is a $C_2$-$C_3$ alkenylidene group.

5. The method according to claim 1, wherein $R^1$ is —CH=CH—.

6. The method according to claim 1, wherein $R^2$ is a $C_1$-$C_8$ alkylidene group.

7. The method according to claim 1, wherein $R^2$ is a $C_1$-$C_3$ alkylidene group.

8. The method according to claim 1, wherein $R^2$ is —CH$_2$—CH$_2$—.

9. The method according to claim 1, wherein the compound of formula (I) is:

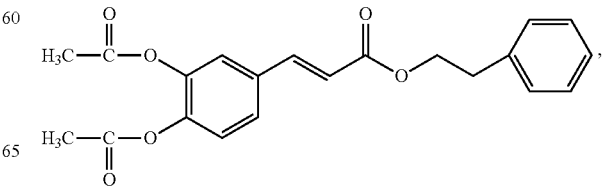

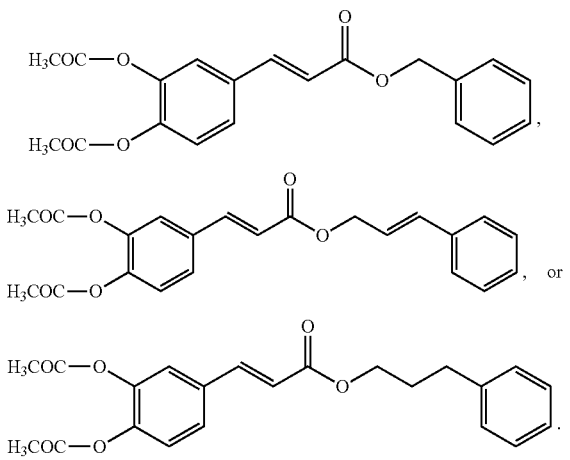
10. A method for preventing and/or treating neoplastic disease, comprising administering to a subject a therapeutically effective amount to a compound of formula (I):
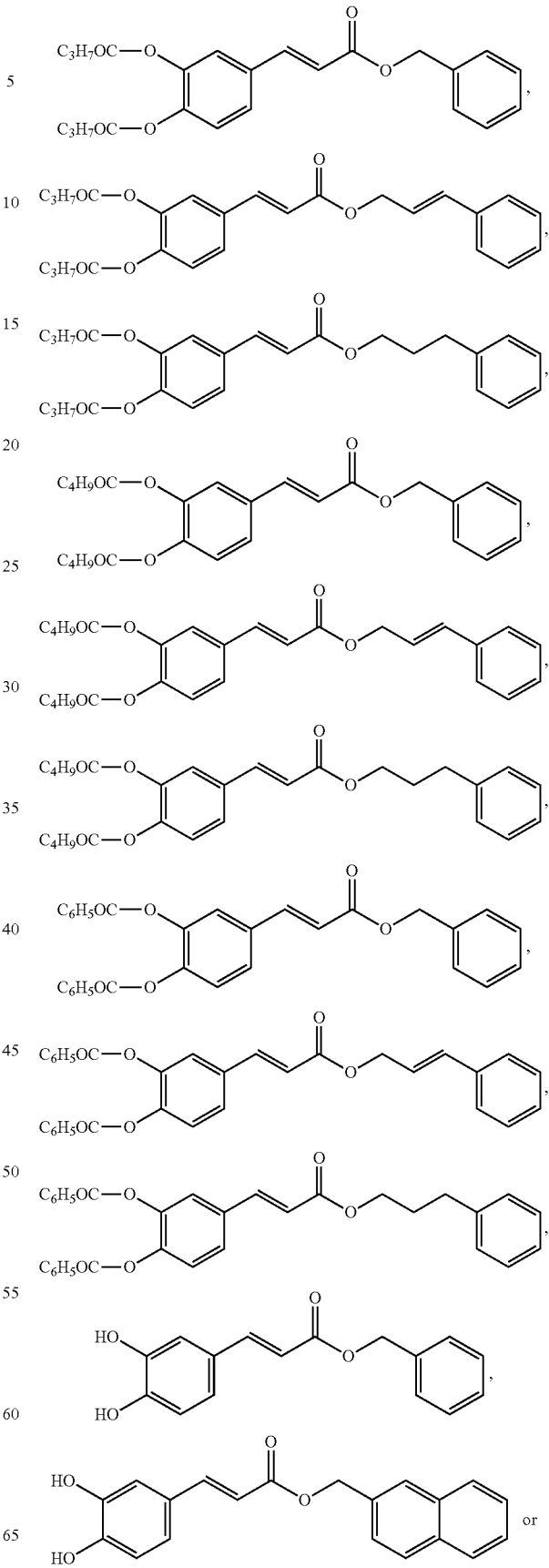

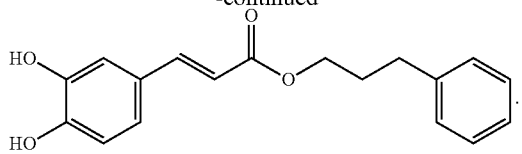

wherein R¹ and R² are each independently $C_1$-$C_8$ alkylidene group or $C_2$-$C_8$ alkenylidene group;
A¹ is 3,4-diacetyl phenyl, and A² is phenyl; and
X and Y are each independently oxygen; and the compound of formula (I) does not comprise phenethyl caffeate.

11. The method according to claim 10, wherein the neoplastic disease comprises solid primary tumors, metastatic tumors or recurrent tumors.

12. The method according to claim 10, wherein R¹ is a $C_2$-$C_8$ alkenylidene group.

13. The method according to claim 10, wherein R¹ is a $C_2$-$C_3$ alkenylidene group.

14. The method according to claim 10, wherein R¹ is —CH=CH—.

15. The method according to claim 10, wherein R² is a $C_1$-$C_8$ alkylidene group.

16. The method according to claim 10, wherein R² is a $C_1$-$C_3$ alkylidene group.

17. The method according to claim 10, wherein R² is —CH$_2$—CH$_2$—.

18. The method according to claim 10, wherein the compound of formula (I) is:

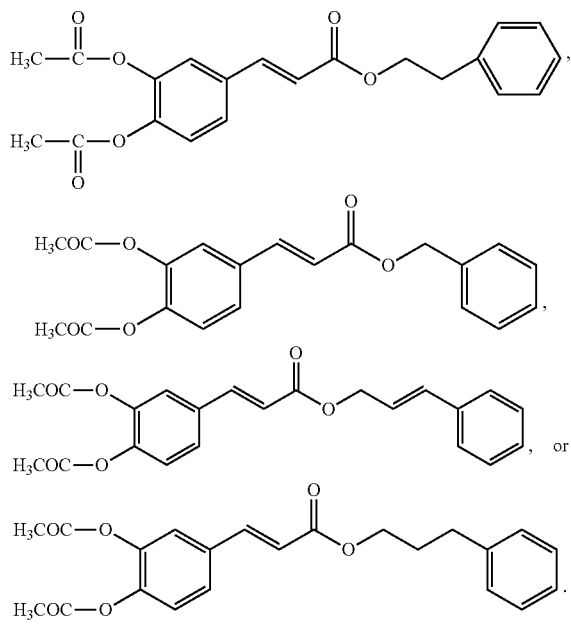

19. A method for inhibiting tumor growth, comprising administering to a subject a therapeutically effective amount of a compound of formula (I):

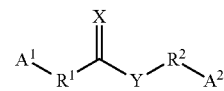

wherein R¹ and R² are each independently $C_1$-$C_8$ alkylidene group or $C_2$-$C_8$ alkenylidene group;
A¹ is 3,4-diacetyl phenyl, and A² is phenyl; and
X and Y are each independently oxygen; and the compound of formula (I) does not comprise phenethyl caffeate.

20. The method according to claim 19, wherein R¹ is a $C_2$-$C_8$ alkenylidene group.

21. The method according to claim 19, wherein R¹ is a $C_2$-$C_3$ alkenylidene group.

22. The method according to claim 19, wherein R¹ is —CH=CH—.

23. The method according to claim 19, wherein R² is a $C_1$-$C_8$ alkylidene group.

24. The method according to claim 19, wherein R² is a $C_1$-$C_3$ alkylidene group.

25. The method according to claim 19, wherein R² is —CH$_2$—CH$_2$—.

26. The method according to claim 19, wherein the compound of formula (I) is:

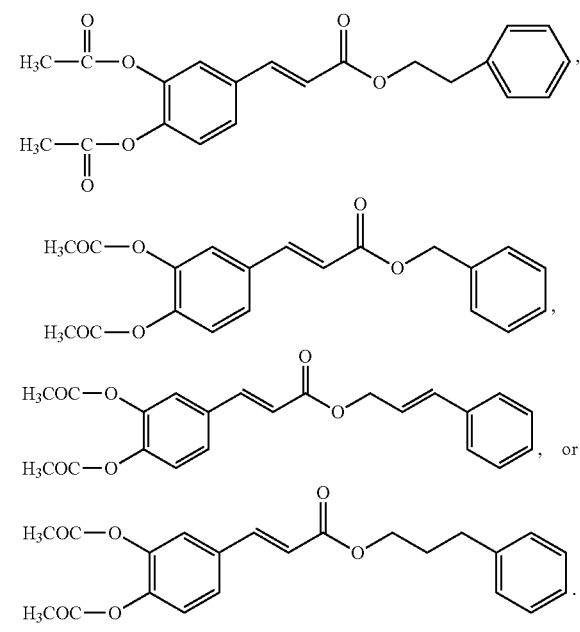

27. The method according to claim 19, wherein the tumor comprises solid primary tumors, metastatic tumors or recurrent tumors.

* * * * *